US00PP13203P2

(12) United States Plant Patent
Patra et al.

(10) Patent No.: US PP13,203 P2
(45) Date of Patent: Nov. 12, 2002

(54) **HIGH YIELDING STABLE PLANT OF *ROSA DAMASCENA*, CALLED 'RANISAHIBA'**

(75) Inventors: Nirmal Kumar Patra; Sushil Kumar; Suman Preet Singh Khanuja; Ajit Kumar Shasney; Alok Kalra; Herikesh Bahadur Singh; Hemendra Pratap Singh; Hasan Tanveer; Ved Ram Singh; Nareshwar Mengi; Dharmendra Kumar Rajput; Mahendra Singh Negi; Neeraj Kumar Tyagi; Paltoo Ram; Vijay Pal Singh; Anand Singh; Birendra Kumar; Jitendra Pal Singh; Vijay Kumar; Shiv Ram Sharma, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/537,188

(22) Filed: Mar. 29, 2000

(51) Int. Cl.[7] ..... A01H 5/00

(52) U.S. Cl. ..... Plt./107

(58) Field of Search ..... Plt./107, 102

*Primary Examiner*—Bruce R. Campell
*Assistant Examiner*—June Hwu
(74) *Attorney, Agent, or Firm*—Birch, Stewart, Kolasch & Birch, LLP

(57) ABSTRACT

The invention provides a novel half-sib damask rose progeny christened as 'Ranisahiba' and characterized by its doubled per se oil content and oil yield, high flower biomass with synchronous flowering and firmly fixed morphophysiological plant-traits.

4 Drawing Sheets

FIELD OF INVENTION

The present invention is related to a super genotype called 'Ranisahiba' a variety of demask rose (*Rosa damascena* var. *bifera*) developed through a comprehensive scheme of half-sib Progeny selection. The plant is a novel plant in the damask rose land race, long grown in Kannauj areas of Uttar Pradesh, India. The variety 'Ranisahiba' readily allows its vegetative multiplication by stem cuttings, its genotype having all morpho-physiological traits including doubled oil yielding ability is firmly fixed after the somatic multiplication so as to give a guarantee for sustained yield advancement.

BACKGROUND OF THE INVENTION

The land race of damask rose, which in recent years has been commercially grown in the Kannauj areas of Uttar Pradesh, India is a major economic crop utilized for its very costly essential oil (Rs.2.25 lakhs per kg) obtained from its freshly harvested flowers by distillation. However, there is a need for its genetic improvement with respect to its problems related to poor oil content and oil yield, irregular bearing in flowers and erratic bearing in individual plants due to blind shoots and barren plants, which are primarily the result of a lack of genetic diversity in the vegetatively derived clones. With a view to solving these problems, our research efforts were directed to the seed progeny selections instead of giving much emphasis on direct clonal selections. Extensive efforts were made to achieve elite out-crossed progeny through controlled half-sib matings in an original large population raised from mixed (dissimilar) stem cuttings collected from the perennial rose plantations in farmers' fields of Kannauj areas of India and establish the obtained elite progeny through productivity trails in contrasting environments of sub tropical plain (Pantnagar) and hill (Purara), India.

OBJECTS

The main object of the invention is to develop a novel rose plant having wide adaptability and capable of growing in sub-tropical and hilly agroclimatic conditions.

Another object is to provide a rose plant yielding essential oil having high geraniol content coupled with a low concentration of undesirable wax component in the essential oil.

A further object is to develop a novel rose plant having globular canopy that allows equal distribution of sunlight to the flowers, thereby producing enhanced flower biomass.

Yet another object is to develop a novel rose plant having high flower yield.

DETAILED DESCRIPTION

Accordingly, the invention provides novel, high essential oil yielding stable plant of *Rosa damascena*, called 'Ranisahiba' having the following firmly fixed new combination of characters, distinct from the known varieties/land races of *R. damascena:* a. Light green stem, red purple (73D) flowers as classified by The "R.H.S. Color Chart," published by The Royal Horticultural Society, 80 Vincent Square, London SWIP 2PE, 1995, globular canopy allowing equal distributon of sunlight to the flowers, that enhances flower biomass,
b. High flower yield,
c. Additional economic yield in off-season, and
d. Yielding essential oil containing 30–35% geraniol, 5–7% geranyl acetate, 4–5% citronellol, 7–8% PE alcohol and 1–3% linalool content, and wax content of about 6–7.1% .

The plant is described herein in detail with reference to the accompanying drawings. The said description should not be construed as limitation on the sphere or scope of the invention.

BRIEF DESCRIPTION OF THE ACCOMPANYING DRAWINGS

In the drawings that accompany, FIG. 1 represents a three year old 'Ranisahiba' plant with profuse bud formations.

FIG. 2 represents red purple (73D) flowers of 'Ranisahiba'.

FIG. 3 represents an oil sample of 'Ranisahiba' (above) and 'Kannauj' (non-patented) control plant; mark the titled bottle with much light oil not freezing at room temperature with less wax component compared to much viscous of control ('Kannauj').

Figure 4:
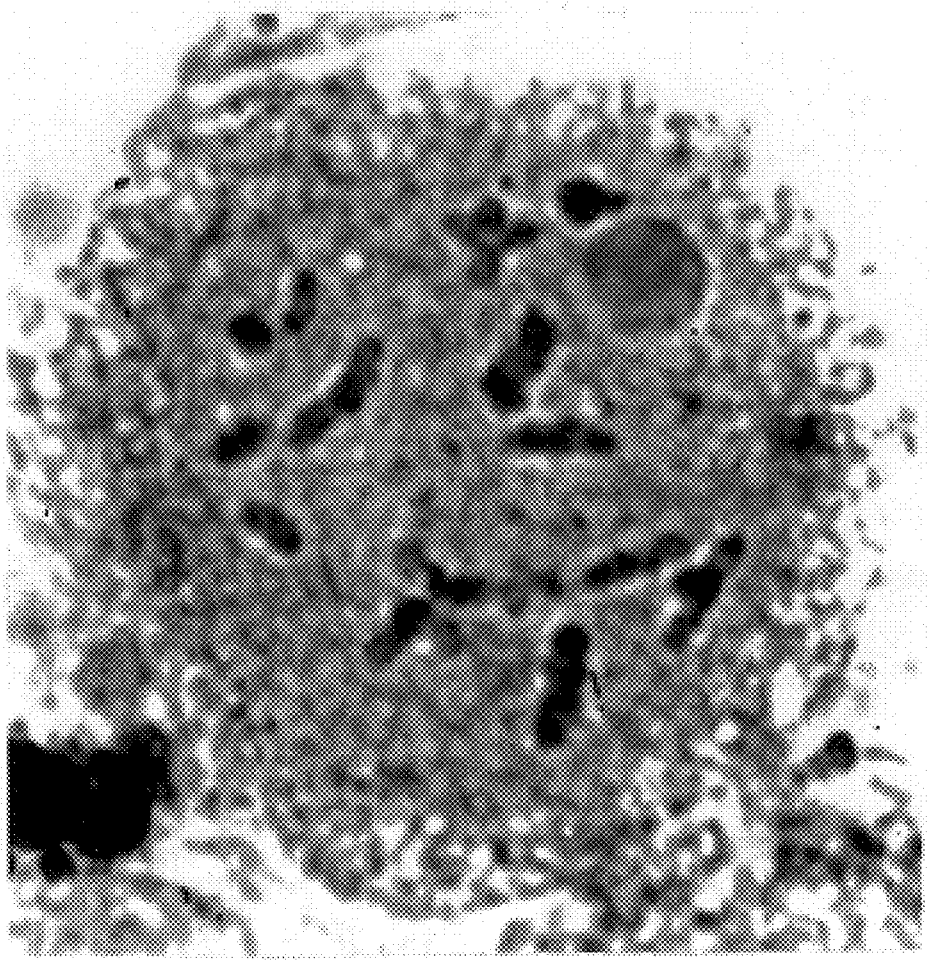
FIG. 4 represents a pollen mother cell showing the chromosome number 2n=4x=28 at the diakinesis stage of meiosis in 'Ranisahiba'.

The new variety 'Ranisahiba' with impressive essential oil productivity is an out-come of strategic half-sib progeny selections for the desirable variant(s) (spontaneous recombinants) of known female plant(s) and unknown male plants(s), clonal multiplication of the desirable variant(s) and their comparative evaluation for morpho-physiological fitnesses leading to the establishment, of the most ideal genotype. The breeding history of 'Ranisahiba' is schematically shown in Table-1. Large efforts made during 1987–91 at CIMAP, Lucknow, India for achieving high ranking out-crossed progeny via the scheme of half-sib matings These involved manual emasculation of the selected known female plants allowed for their natural out crossings with unknown male plants. The original gene pool of 500 plants were raised from mixed (dissimilar) stem cuttings drawn from perennial rose plantations in different farmers' fields of Kannauj areas in Uttar Pradesh, India, and resulted into the development of six half-sib progenies in 1992. Each of these six progenies was subsequently assessed for vegetative multiplication and morphophysiological characteristics. Among the six sets of half-sib progenies, one comprising the highest number of individuals (30 plants against 12–20 in the rest 5 sets) in its clone revealed distinct segregation for an elite variant with robust growth habit, high flower yield, synchronous flowering and much higher per se oil content potential (0.08% as against 0.01–0.04% of the rest 5 half-sibs). This variant, initially named as the strain $V_1$HS-4-18 could be vegetatively multiplied at large scale and assessed for its productivity against three control variety/land races: 'Noorjahan' (the non-patented familiar variety earlier developed by CIMAP), 'Aligarh' non patented control and 'Kannauj' non-patented control in different preliminary/pilot scale yield trials (PYT and PSTs) at the Institute's field station at Pantnagar (a place situated at foot hill area of Uttar Pradesh) and Purara (a valley situated at about 3000 ft ASL at the Bagewar hill of Uttar Pradesh).

The new plant 'Ranisahiba' was reproduced asexually from the original mother plants V1HS-4-18 with the help of hard/semi hard wood stem cuttings (each of 15 cm length), drawn from the latter. The multiplied vegetative progeny ('Ranisahiba') derived through somatic (mitotic) cell division are indistinguishable from the original plant (v1-HS-4-18). As to the character of the area where the plant ('Ranisahiba') has been developed and asexually reproduced, it is situated at the sub-tropical foothill areas of northern India. The soil of the experiment site at Pantnagar was clay-loam in texture, high in organic carbon (1.30%), medium in available P (176.4 kg/ha) and (198.0 kg/ha) with pH7.2. Because the area is located at a latitude of 29° N, longitude of 79.3° E and at the altitude of 244 mts above the mean sea level, it enjoys the minimum temperature ranging from 3–8° C. and maxium temperature ranging from 17–25° C. during winter months. The night temperature during spring (March–April) averaging 10–20° C. with the daily humidity averaging 60–70%, plants do not suffer moisture stress even under the minimum irrigation provision of spring. Indeed the presence of such ideal blooming temperature and high humidity leads to high oil synthesis in the rose flowers.

A point of much interest with this strain is that, besides highly exceeding the three control genotypes for yield in main flowering season (during March–April), out classed the controls for having the capability in generating and additional economic flower and oil yield during off-season of autumn months (September–October). FIG. 2 shows the flowers produced by 'Ranisahiba'. The corresponding result of the yield trials are presented in Table-2, 3 and 4. Per hectare flower and oil yields in Ranisahiba are 52.0 q (i.e.40 q+12 q) and 4 kg (i.e. 3.2 kg+0.8 kg), respectively at Pantnagar (Table 3). Consistent with the yield result of Pantnagar was the yield result from Purara valley, the corresponding figures for flower and oil yield at the Purara hill situation being 53.50 q (i.e. 41 q+12.50 q) and 4.22 kg (i.e. 3.31 kg+0.91 kg) (Table 4). It was evident that the new variety 'Ranisahiba' has wide adaptation and can grow almost equally profitably at sub-tropical and hilly agroclimatic situtation. The comparative performance of 'Ranisahiba' with other varieties is shown in Table 5.

Essential oil samples, prepared from 'Ranisahiba', mentioned three control genotypes and the familiar damask rosa of Bulgaria grown and maintained by us in Purara valley, were examined by gas liquid chromatography (GLC). The oil quality of 'Ranisahiba', though not at par with that of 'Noorjahan' (earlier variety developed through direct clonal selection in the land race of 'Aligarh' (non-patented), Uttar Pradesh), is much superior over the oil of Bulgarian rose. The geraniol in 'Ranisahiba' is 31% as against 18% of the Bulgarian rose. It was also worthwhile to record that the undersirable oil component (C-19) occurs in only very small concentration in 'Ranisahiba' (6.4% against 14.5% of the Bulgarian rose.) Oil of 'Ranisahiba', owning to its less wax component does not freeze in room temperature (20° C.) in winter (FIG. 3 represents an oil sample from 'Ranisahiba').

'Ranisahiba' was further examined for its detailed cytochemo-taxonomical specificies. The corresponding results are given below:

TABLE 1

| | | |
|---|---|---|
| 1. | Genus | Rosa |
| 2. | Species | *damascena* var. *bifera* |
| 3. | Family | Rosaceae |
| 4. | Common name | Damask rose (Kannauj race) |
| 5. | Plant height | 101.10 ± 3.0 cm |
| 6. | Growth habit | Erect, with synchronous branching giving a globular shape to canopy; canopy diameter or growth spread of a three-year old is about 0.80–0.90 m as compared to 0.60–0.70 m of 'Noorjahan'. |
| 7. | Stem | Round with 2.5–3.0 cm girth, prickly with downward pointing thorns color of immature thorns: grey orange (174D) versus 174C of 'Noorjahan'; color of mature thorns: grey orange (174C) versus 174B of 'Noorjahan'), solid, soft texture, woody (old wood color: greenish white (157B) against greeenish white (157A) of 'Noorjahan'and having a hardy texture), cylindrical, green (137B) against yellow green (147B) of the variety 'Noorjahan' (FIG. 2) |

TABLE 1-continued

| | | |
|---|---|---|
| 8. | Leaf | Alternate, compound, pinnate, petiolate, stipulate (stipules adnate to the petiole); leaflets, 5–7 in number, elliptical acute, unicostate, reticulate venation; leaflet length and width: 5.5 cm and 3.2 cm, respectively as against 5.2 cm and 3.3 cm of the variety 'Noorjahan'; Number of dents at the two leaf margins: 54 (for terminal leaflet). 32 (for each of the middle leaflets) and 16 (for the basal leaflet) as against 44, 26 and 22 of 'Noorjahan'; Leaf color, green (139A) on the upper and yellow green (147B) on the lower surface as opposed to the green (137B) and similar yellow green (147B) of 'Noorjahan'; Leaf surface smooth waxy against tough, glossy, and glabrous (non-hairy) versus fragile, rough, wrinkled, and hairy (minute hairs) of 'Noorjahan'. |
| 9. | Inflorescence | Cymose, flowers in clusters (8–10 unicostate, flower weight 2.5 to 3.0 gm, versus 4–6 flowers in each cluster of 'Noorjahan' and a flower weight of 2.5 to 3 gm; lastingness of bloom (flower) is 2–3 days and persistence of bloom (flower) is 3–4 days; flower fragrance is uniquely sweet due to high presence of geraniol component in the essential oil. |
| | Flower diameter | 5.2–5.5 cm, versus 5.5 to 6 cm of 'Noorjahan'; flower bud having a conical shape. |
| | Calyx | Five sepals of green (139C) color (versus 138C of 'Noorjahan'), tough and bold texture, gamosepalous, narrowly lanceolate, calyx-tube persistent, globose ovoid, calyx length 1.1 cm and width 0.5 cm as opposed to 2.3 cm and 0.7 cm of 'Noorjahan'. |
| | Corolla | Comprising 50–70 petals versus 50–55 petals of 'Noorjahan'; petal length 3.2–3.6 cm, petal width 2.2–2.5 cm against 2.3–3.8 cm and 2.4–2.8 cm of 'Noorjahan'; petal color red purple (73A) with red purple (73D) petal base versus a red purple (62C) petal with white petal base of 'Noorjahan'; petal texture thin, tough, and smooth, flower bud red purple (67B) versus 73B of 'Noorjahan'. |
| | Stamen | 78–90 in number versus 70–80 of 'Noorjahan', anthers grey red (181C) versus yellow orange (22A) of 'Noorjahan', inserted on the flower disk; anther length 1.5–2.0 mm versus 1.0–1.5 mm of 'Noorjahan'; Filament yellow orange (22B) versus yellow (11C) of 'Noorjahan'; filament length 5.0–5.5 mm versus 4.0–5.0 mm of 'Noorjahan'; pistils of numerous number. |
| | Carpels | Many carpels, apocarpous (found in the base of the calyx-tube), Stigma thickened |
| | Pollen | Color orange red (32D) versus yellowish orange (81D) of 'Noorjahan'. |
| | Style | Length of 6.0–7.0 mm versus 5.0–6.0 of 'Noorjahan'. |
| 10. | Fruit | Pome (i.e., a small indehiscent many seeded fruit), grey red (181C), fleshy, elongated, avoid; Fruit originating from the cup-like receptacle bearing the sepals, petals and stamens its rim and enclosing the carpels and measuring 0.9 cm × 1.2 cm with fruit index (w/l) 1.3 versus 1.2 cm × 0.7 cm and fruit index 0.58 of 'Noorjahan'; the length of receptacle is 10.0–11.0 as in 'Noorjahan'; receptacle texture thick and bold with inner soft tissues. |
| 11. | Oil content in the fresh flower | 0.8% as against 0.04% of the variety 'Noorjahan' and 0.02% of Bulgarian rose. |
| 12. | Oil quality | |
| | Geraniol content | 30.0–35.0% (against 18.20 of Bulgarian rose) |
| | Geranyl acetate | 5.4–7.0% (against 1.6% of Bulgarian rose) |
| | citronellol | 4.6–5.0% (against 33.3% of Bulgarian rose) |
| | PE alcohol | 7.0–8.0% (against 1.4% of Bulgarian rose) |
| | Linalool | 1.1–2.5% (against 2.2% of Bulgarian rose) |
| | Wax component (C-19) | 6.0–7.1% (against 14.5% of Bulgarian rose) |

The genotype 'Ranisahiba' is a perennial shrubs with upright prickly shoots. The synchronous branching of shoots gives a globular canopy of the plant. The flowers bloom largely synchronously leading to brevity in flower picking. The chromosome number is 2n=4x=28 (tetraploid) FIG. 4 represents a pollen cell of 'Ranisahiba' showing chromosome number is 2n=4x=28 at diakinesis stage.

Stability and Plant Hardness

'Ranisahiba' was assessed for its stability in yield for five years (1994–99) in two contrasting places: Pantnagar (a sub-tropical plain) and Purara (a tempercate hill). The obtained results revealed its high stability and adaptation over the environments. As 'Ranisahiba' is vegetatively propagated by stem cuttings, its morpho-physiological traits including oil yield are firmly fixed. (Further details given in Table -1).

The plant of the invention 'Ranisahiba' is frost sensitive revealing withering of the shoot tips in its unpruned plants furing chilling winter (0–5° C.) of December and January, especially in the places at higher altitudes (>500 m). To overcome the environmental hostility of the chilling winter, the plant 'Ranisahiba' like the others needs deep pruning during first week of December. The mature plant parts after pruning during first week of December are resistant to frosting and start sprouting during mid-January after a brief period of remaining dormant at both hill and foot hill situations. However, it is worthwhile to mention that sprouting of shoots as well as flower bud formation in 'Ranisahib' are early (15 days and 20 days earlier respectively) as compared to the normal cultivars. The flower buds in profuse number are observed in 'Ranisahiba' at the foot hill area during first week of March as against that during last week of March in 'Noorjahan' and others. The early sprouting behavior in articular is a major physiological 'marker' to identify some winter hardiness in the new genotype 'Ranisahiba'.

As evident from the morpho-physiology the plant of 'Ranisahiba' is distinct from its mother 'Kannauj' control as well as the other two controls: the variety 'Noorjahan' and 'Aligarh' land race. The mentioned globular plant canopy is the major morphological "marker" for identifying 'Ranisahiba' from known varieties/land races. Globular canopy allows equal distribution of sunlight to the flowers, leading to enhanced flower biomass. The novelty of the invention in that 'Ranisahiba', besides being superior to the existing rose varieties and land races for flower yield, distinctly outclasses all existing rose genotypes/land races by having high oil content and oil yield and high geraniol content coupled with least concentration of undesirable wax component in the essential oil.

TABLE 2

Comparative performances of the strain: Ranisahiba and other variety/land races of damask rose in PYT (1994–95) at Field station, Pantnagar (Plot Size: 5 m × 2 m)

| | Performance in | | | |
|---|---|---|---|---|
| | 'Noorjahan' (Control) | | 'Aligarh' (Control) | |
| Plant traits | MS | OS | MS | OS |
| Plant height (cm) | 101.10 | — | 110.60 | — |
| Stem girth (cm) | 2.20 | — | 2.10 | — |
| No. of Primary branches | 6.60 | — | 7.00 | — |
| No. of flowers/plant | 148.12 | — | 137.5 | — |

TABLE 2-continued

Comparative performances of the strain: Ranisahiba and other variety/land races of damask rose in PYT (1994–95) at Field station, Pantnagar (Plot Size: 5 m × 2 m)

| | | | | |
|---|---|---|---|---|
| No. of flowers/cluster | 8.10 | — | 7.20 | — |
| Single flower Weight (g) | 2.40 | — | 2.00 | — |
| Flower yield/plot/10 $m^2$ (kg) | 3.60 | — | 2.75 | — |
| Flower yield/ha (q) | 35.92 | — | 27.35 | — |
| Oil content (%) | 0.04 | — | 0.02 | — |
| Oil yield/ha (kg) | 1.42 | — | 0.54 | — |

| | 'Kannauj' (Control) | | 'Ranisahiba' | |
|---|---|---|---|---|
| Plant traits | MS | OS | MS | OS |
| Plant height (cm) | 130.50 | 132.10 | 104.5 | 150.8 |
| Stem girth (cm) | 2.26 | 1.87 | 2.15 | 2.80 |
| No. of Primary branches | 7.40 | 2.90 | 8.70 | 5.00 |
| No. of flowers/plant | 135.40 | 7.50 | 195.40 | 44.10 |
| No. of flowers/cluster | 7.10 | 1.60 | 9.12 | 4.50 |
| Single flower Weight (g) | 2.00 | 2.40 | 2.00 | 2.40 |
| Flower yield/plot/10 $m^2$ (kg) | 2.67 | 0.25 | 4.10 | 1.18 |
| Flower yield/ha (q) | 26.65 | 2.05 | 39.96 | 11.72 |
| Oil content (%) | 0.02 | 0.02 | 0.08 | 0.07 |
| Oil yield/ha (kg) | 0.50 | 0.038 | 3.17 | 0.80 |

MS = Main season (March–April)
OS = Off season (Sept.–Oct.)

TABLE 3

Comparative performances of the strain: Ranisahiba and other variety/land races of damask rose in PYT (1994–95) at Field station, Pantnagar (Plot Size: 5 m × 2 m)

| | Performance in | | | |
|---|---|---|---|---|
| | 'Noorjahan' (Control) | | 'Aligarh' | |
| Plant traits | MS | OS | MS | OS |
| Plant height (cm) | 101.10 | — | 110.60 | — |
| Stem girth (cm) | 2.20 | — | 2.10 | — |
| No. of Primary branches | 6.60 | — | 7.00 | — |
| No. of flowers/plant | 148.12 | — | 137.5 | — |
| No. of flowers/cluster | 8.10 | — | 7.20 | — |
| Single flower Weight (g) | 2.40 | — | 2.00 | — |
| Flower yield/plot/10 $m^2$ (kg) | 3.60 | — | 2.75 | — |
| Flower yield/ha (q) | 35.92 | — | 27.35 | — |
| Oil content (%) | 0.04 | — | 0.02 | — |
| Oil yield/ha (kg) | 1.42 | — | 0.54 | — |

| | 'Kannauj' (Control) | | 'Ranisahiba' | | C.D. (5%) |
|---|---|---|---|---|---|
| Plant traits | MS | OS | MS | OS | for MS |
| Plant height (cm) | 130.50 | 132.10 | 104.5 | 150.8 | 7.00 |
| Stem girth (cm) | 2.26 | 1.87 | 2.15 | 2.80 | (NS) |
| No. of Primary branches | 7.40 | 2.90 | 8.70 | 5.00 | 0.68 |
| No. of flowers/plant | 135.40 | 7.50 | 195.40 | 44.10 | 8.44 |
| No. of flowers/cluster | 7.10 | 1.60 | 9.12 | 4.50 | 0.29 |
| Single flower Weight (g) | 2.00 | 2.40 | 2.00 | 2.40 | 0.22 |
| Flower yield/plot/10 $m^2$ (kg) | 2.67 | 0.25 | 4.10 | 1.18 | 0.23 |
| Flower yield/ha (q) | 26.65 | 2.05 | 39.96 | 11.72 | 2.75 |
| Oil content (%) | 0.02 | 0.02 | 0.08 | 0.07 | 0.0041 |
| Oil yield/ha (kg) | 0.50 | 0.038 | 3.17 | 0.80 | 0.097 |

MS = Main season (March–April)
OS = Off season (Sept.–Oct.)

TABLE 4

Comparative performances of the strain: Ranisahiba and other variety/land races of damask rose in PST (1998–99) at Field station, Purura (Plot Size: 10 m × 5 m)

| | Performance in | | | |
|---|---|---|---|---|
| | 'Noorjahan' (Control) | | 'Aligarh' (Control) | |
| Plant traits | MS | OS | MS | OS |
| Plant height (cm) | 101.20 | — | 109.50 | — |
| Stem girth (cm) | 2.24 | — | 2.10 | — |
| No. of Primary branches | 7.20 | — | 7.30 | — |
| No. of flowers/plant | 153.42 | — | 142.5 | — |
| No. of flowers/cluster | 8.70 | — | 8.10 | — |
| Single flower Weight (g) | 2.52 | — | 2.00 | — |
| *Flower yield plot (kg)/ 50 $m^2$ | 19.25 | — | 15.50 | — |
| Flower yield/ha (q) | 38.10 | — | 30.60 | — |
| Oil content (%) | 0.04 | — | 0.02 | — |
| Oil yield/ha (kg) | 1.54 | — | 0.63 | — |

| | 'Kannauj' (Control) | | 'Ranisahiba' | | C.D. |
|---|---|---|---|---|---|
| Plant traits | MS | OS | MS | OS | (5%) |
| Plant height (cm) | 132.20 | 133.10 | 103.40 | 151.60 | 6.27 |
| Stem girth (cm) | 2.28 | 1.92 | 2.15 | 2.80 | 0.12 |
| No. of Primary branches | 7.50 | 3.00 | 8.90 | 5.10 | 0.26 |
| No. of flowers/plant | 140.50 | 9.20 | 205.40 | 50.70 | 7.57 |
| No. of flowers/cluster | 7.63 | 2.10 | 9.85 | 5.30 | 0.23 |
| Single flower Weight (g) | 2.10 | 2.53 | 2.00 | 2.54 | 0.18 |
| *Flower yield plot (kg)/ 50 $m^2$ | 14.20 | 1.15 | 20.75 | 6.40 | 1.71 |
| Flower yield/ha (q) | 28.12 | 2.11 | 41.00 | 12.50 | 1.29 |
| Oil content (%) | 0.02 | 0.018 | 0.08 | 0.07 | 0.0045 |
| Oil yield/ha (kg) | 0.55 | 0.04 | 3.31 | 0.91 | 0.14 |

MS = Main season (March–April)
OS = Off season (Sept.–Oct.)

TABLE 5

Comparative performances of the strain: Ranisahiba and other variety/land races of damask rose in PST (1998–99) at Field station, Pantnagar (Plot Size: 5 m × 2 m)

| | Performance in | | | |
|---|---|---|---|---|
| | 'Noorjahan' (Control) | | 'Aligarh' (Control) | |
| Plant traits | MS | OS | MS | OS |
| Plant height (cm) | 104.10 | — | 112.60 | — |
| Stem girth (cm) | 2.25 | — | 2.12 | — |
| No. of Primary branches | 7.00 | — | 7.20 | — |
| No. of flowers/plant | 151.13 | — | 140.8 | — |
| No. of flowers/cluster | 8.13 | — | 7.60 | — |
| Single flower Weight (g) | 2.50 | — | 2.00 | — |
| Flower yield/plot (kg) | 18.90 | — | 14.10 | — |
| Flower yield/ha (q) | 37.78 | — | 28.16 | — |
| Oil content (%) | 0.04 | — | 0.02 | — |
| Oil yield/ha (kg) | 1.51 | — | 0.56 | — |

| | Performance in | | | | |
|---|---|---|---|---|---|
| | 'Kannauj' | | 'Ranisahiba' | | C.D. |
| Plant traits | MS | OS | MS | OS | (5%) |
| Plant height (cm) | 134.80 | 135.40 | 106.50 | 153.70 | 6.99 |
| Stem girth (cm) | 2.27 | 1.90 | 2.20 | 2.82 | (NS) |

TABLE 5-continued

| | | | | | |
|---|---|---|---|---|---|
| No. of Primary branches | 7.50 | 3.00 | 8.80 | 5.00 | 0.33 |
| No. of flowers/plant | 138.40 | 8.50 | 200.30 | 48.50 | 9.71 |
| No. of flowers/cluster | 7.33 | 1.80 | 9.33 | 5.00 | 0.34 |
| Single flower Weight (g) | 2.00 | 2.50 | 2.00 | 2.50 | 0.12 |
| Flower yield/plot (kg) | 13.84 | 1.06 | 20.01 | 6.07 | 4.24 |
| Flower yield/ha (q) | 27.67 | 2.11 | 40.03 | 12.13 | 3.01 |
| Oil content (%) | 0.02 | 0.02 | 0.08 | 0.07 | 0.0031 |
| Oil yield/ha (kg) | 0.04 | 0.04 | 3.21 | 0.88 | 0.103 |

MS = Main season (March–April)
OS = Off season (Sept.–Oct.)

We claim:

1. A novel, high yielding stable plant of *Rosa damascena*, designated 'Ranisahiba' as described and illustrated, and having the following firmly fixed new combination of characteristics, distinct from the known varieties/land races of *R. damascena:*

(a) Light green stem, red purple (73D) flowers, globular canopy allowing equal distribution of sunlight to the flowers, that enhances flower biomass;

(b) High flower yield;

(c) Additional economic yield off-season;

(d) Yielding oil containing 30–35% geraniol content, 5–7% geranyl acetate content, 4–5% citronellol, 7–8% PE alcohol and 1–3% linalool content; and (e) High geraniol content coupled with wax content of about 6–7.1%.

* * * * *